United States Patent [19]

Harandi et al.

[11] Patent Number: 4,857,667
[45] Date of Patent: Aug. 15, 1989

[54] SYSTEM FOR CONVERSION OF CRUDE OXYGENATE TO GASOLINE WITH FEEDSTOCK EXTRACTION

[75] Inventors: Mohsen N. Harandi, Sewell; Hartley Owen, Belle Mead, both of N.J.

[73] Assignee: Mobil Oil Corporation, New York, N.Y.

[21] Appl. No.: 105,425

[22] Filed: Oct. 7, 1987

Related U.S. Application Data

[63] Continuation-in-part of Ser. No. 43,718, Apr. 29, 1987, Pat. No. 4,709,113.

[51] Int. Cl.$^4$ .............................................. C07C 1/20
[52] U.S. Cl. .................................. 585/403; 585/503; 585/469; 585/636; 585/640; 585/920; 585/921; 585/408
[58] Field of Search ............... 585/640, 733, 469, 639, 585/408, 754, 403, 503, 920, 921, 636; 422/211, 234, 235, 225

[56] References Cited

U.S. PATENT DOCUMENTS

| | | | |
|---|---|---|---|
| 4,497,968 | 2/1985 | Wright et al. | 585/304 |
| 4,513,156 | 4/1985 | Tabak | 585/329 |
| 4,709,113 | 11/1987 | Harandi et al. | 585/640 |
| 4,788,042 | 11/1988 | Marsh et al. | 585/403 |
| 4,788,369 | 11/1988 | Marsh et al. | 585/403 |

Primary Examiner—Asok Pal
Attorney, Agent, or Firm—Alexander J. McKillop; Charles J. Speciale; L. G. Wise

[57] ABSTRACT

Apparatus for converting crude aqueous oxygenate feedstock, such methanol or the like, to liquid hydrocarbons in contact with a medium pore shape selective crystalline acid zeolite catalyst, such as HZSM-5. In a preferred embodiment, the novel technique comprises means for: (a) contacting a crude methanol feedstock containing a minor amount of water with a liquid hydrocarbon extraction stream under extraction conditions favorable to selective extraction of the methanol, thereby providing an extract liquid stream rich in methanol and an aqueous raffinate stream lean in methanol; (b) charging the extracted methanol substantially free of water to said reaction zone under process conditions to convert substantially all methanol to hydrocarbons; (c) cooling reaction effluent to recover aqueous liquid byproduct stream, gas rich in $C_2^-$ hydrocarbons, liquid rich in $C_3$-$C_4$ hydrocarbons and $C_5^+$ liquid hydrocarbons; and (d) contacting crude methanol feedstock with at least a portion of the liquid hydrocarbons employed as extraction liquid.

6 Claims, 5 Drawing Sheets

SYSTEM FOR CONVERSION OF CRUDE OXYGENATE TO GASOLINE WITH FEEDSTOCK EXTRACTION

REFERENCE TO COPENDING APPLICATION

This application is a continuation-in-part of U.S. patent application Ser. No. 043,718, filed Apr. 29, 1987, now U.S. Pat. No. 4,709,113 incorporated herein by reference.

FIELD OF THE INVENTION

This invention relates to process equipment and operating techniques for converting methanol and/or related oxygenated organic compounds to gasoline boiling range hydrocarbons. In particular, the invention relates to a system for removing water from crude aqueous methanol feedstock or the like prior to catalytic reaction in a MTG (methanol to gasoline) reactor.

BACKGROUND OF THE INVENTION

Processes for converting lower oxygenates such as methanol to hydrocarbons are known and have become of great interest in recent times because they offer an attractive way of producing liquid hydrocarbon fuels, especially gasoline, from sources which are not of liquid petroleum origin. In particular, they provide a way by which methanol can be converted to gasoline boiling range products in good yields. The methanol, in turn, may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contain a significant amount of water, usually in the range of 4 to 20 wt %.

The conversion of methanol and other lower aliphatic oxygenates to hydrocarbon products may take place in a fixed bed process as described in U.S. Pat. Nos. 3,998,899; 3,931,349 and 4,035,430. Fluidized bed catalysis has been described in U.S. Pat. Nos. 4,251,484 (Daviduk et al) and 4,513,160 (Avidan and Kam). In the fixed bed process, the methanol is usually first subjected to a dehydrating step, using a catalyst such as gamma-alumina, to form an equilibrium mixture of methanol, dimethyl ether (DME) and water. This mixture is then passed at elevated temperature and pressure over a catalyst such as ZSM-5 zeolite for conversion to the hydrocarbon products which are mainly in the range of light gas to gasoline. Water may be removed from the methanol dehydration products prior to further conversion to hydrocarbons and the methanol can be recycled to the dehydration step, as described in U.S. Pat. No. 4,035,430. Removal of the water is desirable because the catalyst may tend to become deactivated by the presence of excess water vapor at the reaction temperatures employed; but this step is not essential.

In the operation of an adiabatic fixed bed process, a major problem is thermal balance. The conversion of the oxygenated feed stream (methanol, DME) to the hydrocarbons is a strongly exothermic reaction liberating approximately 1480 kJ. (1400 Btu) of heat per kilogram of methanol. In an uncontrolled adiabatic reactor this would result in a temperature rise which would lead to extremely fast catalyst aging rates or even to damage to the catalyst. Furthermore, the high temperatures which might occur could cause undesirable products to be produced or the product distribution could be unfavorably changed. It is therefore necessary that some method should be provided to maintain the catalyst bed within desired temperature limits by dissipating the heat of the reaction.

One method is to employ a light gas portion of the hydrocarbon product as recycle, as described in U.S. Pat. No. 3,931,349 (Kuo). Typically, cooled light hydrocarbon gas, rich in methane, ethane, etc., is separated from the $C_5+$ gasoline and $C_3-C_4$ LPG products, re-compressed and reheated before being mixed with the reactant feedstream entering the bed of conversion catalyst. Although effective in controlling bed temperature, the expense of cooling the recycle gas, compressing it and re-heating it add to the cost of the conversion.

Typically the crude methanol feestock employed in MTG processes contains about 4 to 20 wt % water as the principal impurity. Excessive water not only contributes to catalyst deactivation, but also requires larger volume equipment to handle the increased throughput. Various proposals have been put forth for reducing the water content of crude methanol, for instance the distillation system described by Mao et al in copending U.S. patent application Ser. No. 823,153, filed Jan 27, 1986, incorporated by reference.

It is main object of the present invention to provide a novel and economic technique for removing excess water from crude MTG feedstocks, including novel unit operations and equipment for treating these oxygenate feedstocks.

SUMMARY OF THE INVENTION

Improved apparatus is provide for converting crude aqueous methanol feedstock to gasoline boiling range hydrocarbons in contact with a medium pore shape selective crystalline acid zeolite catalyst. The improvement comprises means for contacting the aqueous methanol feedstock with a liquid hydrocarbon extractant under liquid extraction conditions, means for recovering an aqueous phase containing the major amount of water and a portion of methanol introduced with the feedstock; means for recovering an organic extract phase comprising the hydrocarbon extractant and methanol introduced in the feedstock; and reactor means for converting the extracted methanol at elevated temperature under catalytic reaction conditions to produce predominantly gasoline range liquid hydrocarbons and a minor amount of $C_3-C_4$ hydrocarbons. The liquid hydrocarbons and/or $C_3-C_4$ may be passed to the extraction step to provide a selective composition for removing methanol from the crude feedstream. This technique is adapted for continuous process conditions.

These and other objects and features of the invention will be understood from the following description and in the drawing.

DRAWING

FIG. 1 of the drawing is a schematic process flow-sheet depicting the present invention;

DETAILED DESCRIPTION

The present invention is useful for the conversion of methanol. The hydrocarbon product will be a hydrocarbon mixture ranging from light gas to heavier fractions, but will generally be concentrated in the gasoline boiling range ($C_5$-220°C.). The MTG process is particularly useful in the catalytic conversion of methanol and its corresponding ether to normally liquid hydrocarbons in the $C_5$-$C_{10}$ range. For convenience, the process will be described below with reference to such a specific methanol/DME conversion process; although it should be remembered that the principles are applicable to a broader range of conversions.

When methanol is used as the starting material for the process it is preferred to subject it to an initial dehydration step to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred.

Figure 1:
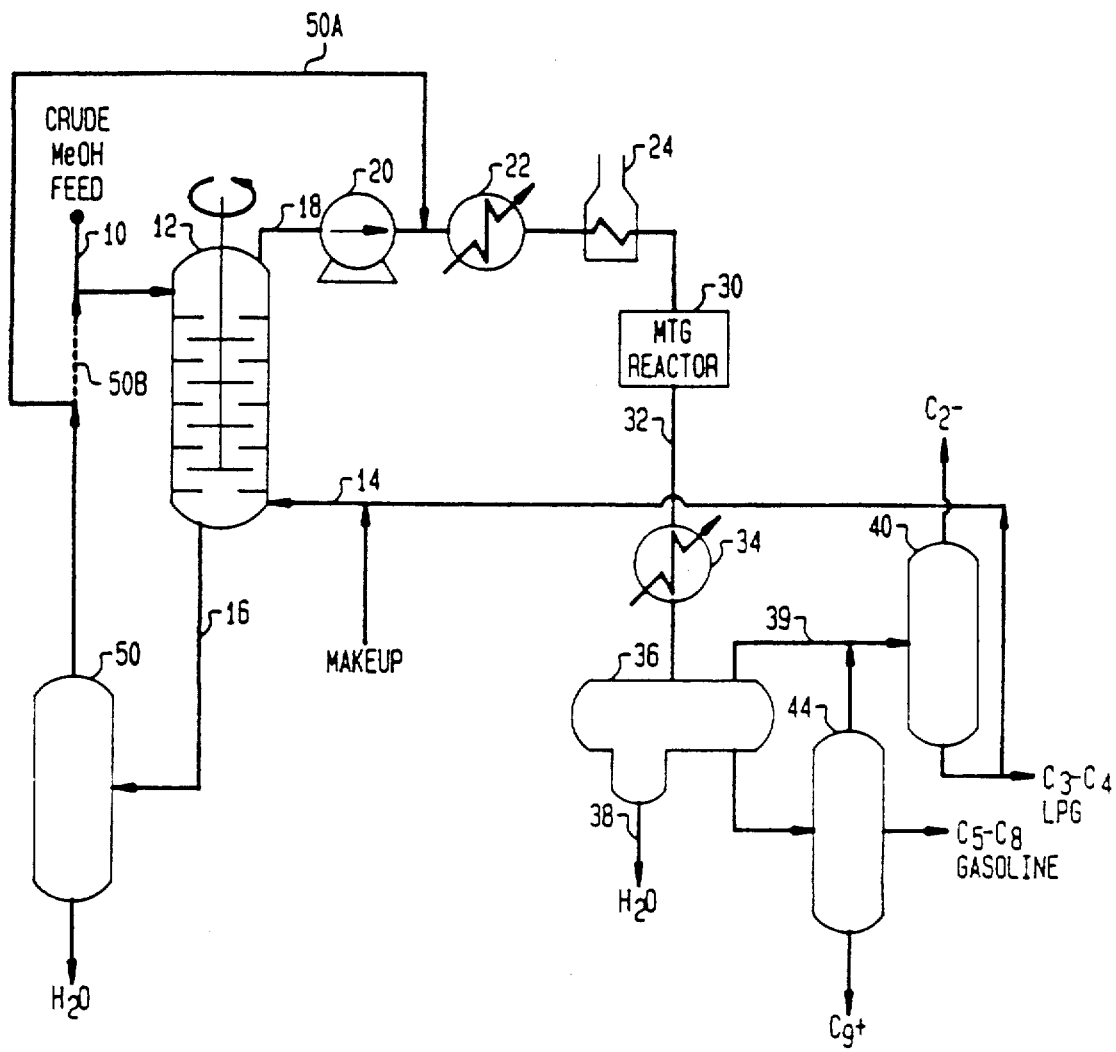

Referring to FIG. 1 of the drawing, crude methanol (MeOH) feedstock is introduced via conduit 10 to a top inlet of extraction unit 12, where it is contacted under liquid extraction conditions with a countercurrent stream of hydrocarbon liquid extractant introduced at a bottom inlet via conduit 14. An aqueous raffinate phase containing a major amount of the water present in the crude feedstock is withdrawn via conduit 16. The lighter organic extract phase containing hydrocarbon extraction solvent and a significant amount of feedstock methanol is recovered from extraction unit 12 via conduit 18, pressurized by pump means 20, passed through heat exchanger 22, furnace 24 and introduced at elevated temperature and process conditions suitable for conversion of substantially all of the methanol in contact with the MTG catalyst in reactor system 30. The crude feedstock mixture of methanol may be fed directly to a fixed bed MTG (methanol to gasoline) catalytic reactor. From the reactor system 30, the effluent product stream leaves via line 32 to a heat exchanger condenser 34, and is passed as a three-phase mixture to a primary phase separator 36. The temperature and pressure of the separator are maintained such that the products are split into three separate streams. The byproduct water is recovered via line 38. The light hydrocarbon gas phase is passed via line 39 to a deethanizer tower or similar gas separation unit for recovery of $C_2-$ fuel gas byproduct and LPG rich in $C_3$-$C_4$ hydrocarbons, especially propane and butanes, which may be further fractionated to recover isobutane or other components thereof. The condensed liquid hydrocarbon stream from separator unit 38 is further fractionated in tower 44 to provide the $C_5$-$C_8$ gasoline product stream, a $C_9+$ aromatics rich heavy gasoline stream and a $C_4-$ overhead vapor stream, which is combined with vapor stream 39 flowing to the deethanizer tower 40. A recycle $C_3$-$C_4$ stream including at least a portion of LPG hydrocarbons recovered from the process reactor effluent is sent via conduit 14 to use as extractant liquid, along with any added propane or other makeup hydrocarbon liquid added to the process extractant stream.

The aqueous raffinate stream 16 consists essentially of water, partitioned methanol and a trace of hydrocarbon. This may be recovered and fractionated in tower 50 to provide a methanol-rich auxiliary feedstream 50A. Alternatively this may be combined with crude feedstock in conduit 10.

EXTRACTION UNIT OPERATION

Extraction conditions may be varied depending upon water content of crude methanol feedstock and the required water-oxygenate separation. A typical crude feedstock material is methanol containing about 4 to 17% by weight water. The extraction unit 12 can be designed as a stirred multi-stage vertical extraction column adapted for continuous operation at elevated pressure. Any suitable extraction equipment may be employed, including cocurrent, cross-current or single stage contactors, wherein the liquid methanol feedstock is intimately contacted with a substantially immiscible liquid hydrocarbon solvent, which may be a mixture of $C_3+$ aliphatic components or relatively pure propane, butane, etc. This unit operation is described in *Kirk-Othmer Encyclopedia of Chemical Technology* (Third Ed.), 1980, pp. 672–721. Other equipment for extraction is disclosed in U.S. Pat. Nos. 4,349,415 (DeFilipi et al) and 4,626,415 (Tabak). The methanol extraction step can be performed advantageously in a countercurrent multistage design, such as a simple packed column, rotating disk column, agitated column with baffles or mesh, or a series of single stage mixers and settlers.

Figure 2:
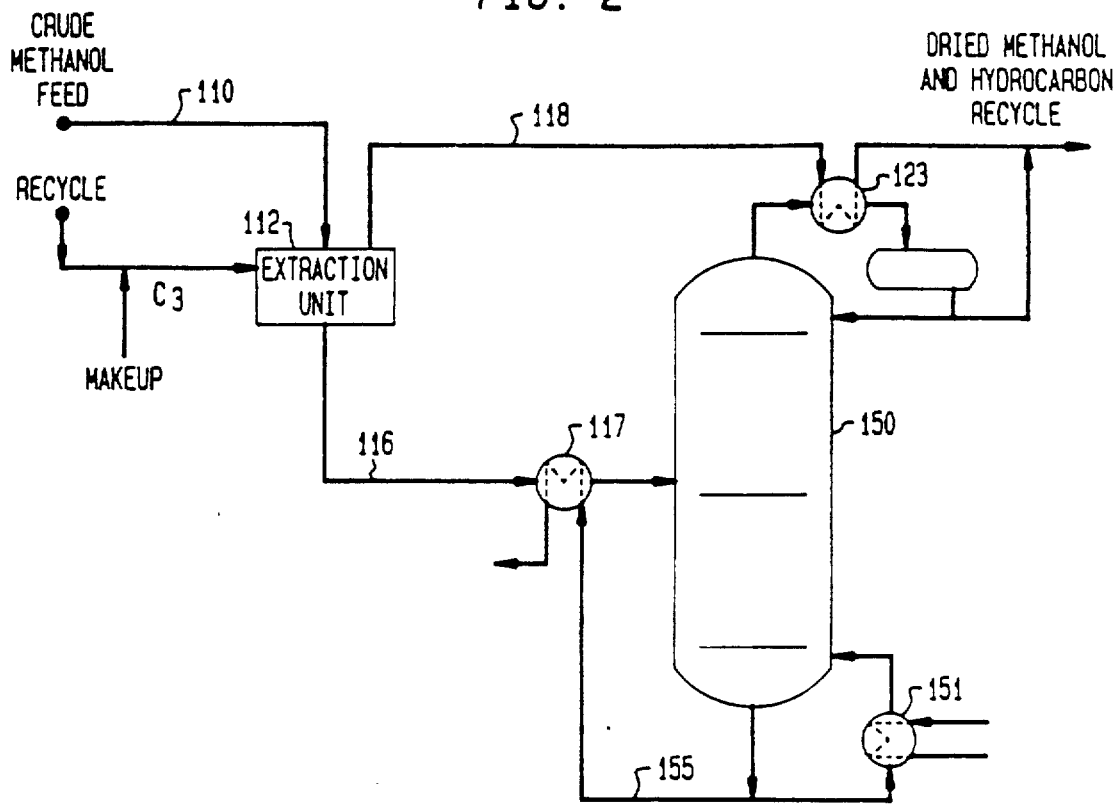
FIG. 2 is a flow diagram of an extraction and methanol dewatering subsystem using $C_3$ alkane extractant.

As an example of crude methanol dewatering technique, FIG. 2 shows an integrated extraction and distillation operation with thermal recovery, employing similar ordinal numbers for corresponding elements in FIG. 1. In this example crude methanol containing about 17 wt % is fed via inlet 110 to extraction unit 112 at a flow rate of 16364 moles MeOH + 6080 moles $H_2O$, where it is contacted with 89776 moles of $C_3$ (propane) hydrocarbon at a temperature of 43C. The extract phase containing 9596 moles of MeOH, 325 moles $H_2O$ (less than 2 wt %), and 89560 moles $C_3$ hydrocarbon is passed via conduit 118, heat exchanger 123 and combined with distilled methanol to provide a reactor system feedstream containing 16357, 1175 and 89776 moles, respectivlely. Raffinate stream 116, containing 6768 moles MeOH, 5755 moles $H_2O$, and 216 moles $C_3$ is heated in exchanger 117 and introduced to distillation tower 150 for further enrichment of the methanol overhead, which is condensed in exchanger 123 for reflux and reactor feed. Distillation bottoms are reboiled in exchanger 151 and a wastewater stream 155 is recovered containing about 4905 moles of water and 7 moles of MeOH.

The solubility of methanol in hydrocarbons coupled with the insolubility of hydrocarbons in water makes extraction a viable step in methanol dewatering. The heavy liquid raffinate phase, consisting mostly of water and methanol (less than 4 wt. % hydrocarbon), is distilled to recover unextracted MeOH and partitioned hydrocarbon. By implementing extraction first, the feed to the distillation column is significantly reduced, thus reducing tower diameter, reboiler duty and overhead condenser duty.

Figure 3:
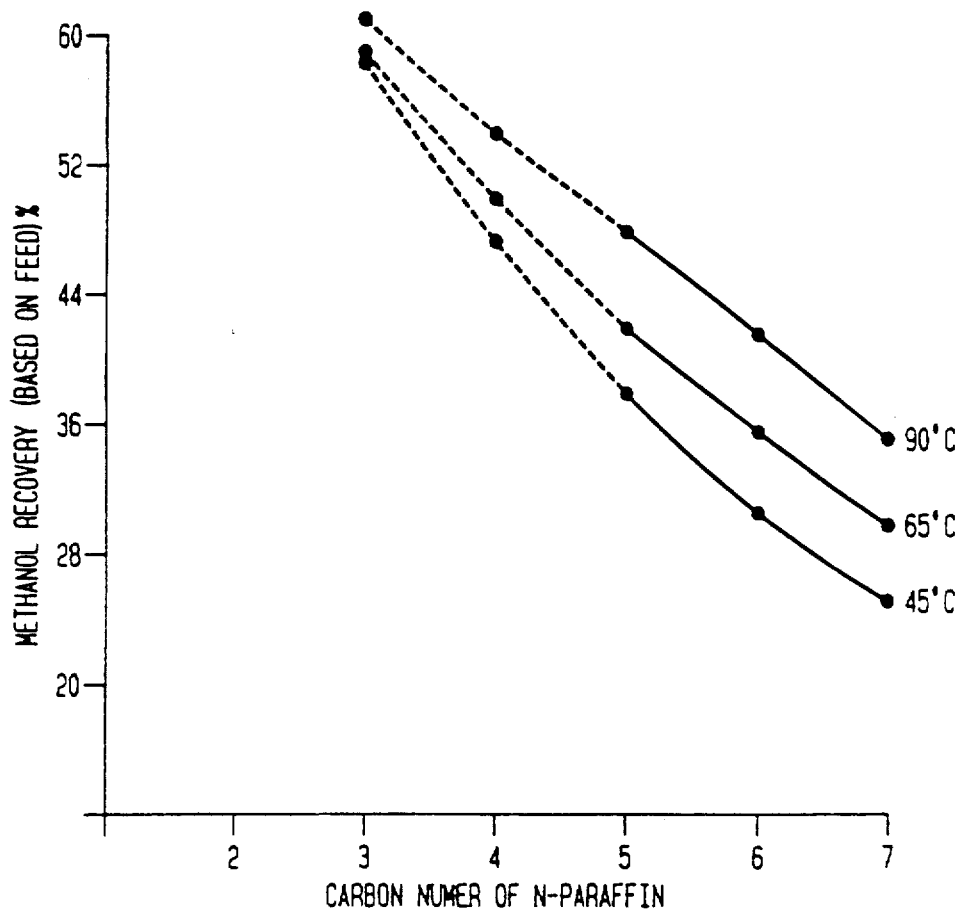
FIG. 3 is a graphic plot of methanol recovery vs. carbon number of n-alkane extractant, showing extraction temperature as parameter.
Figure 4:
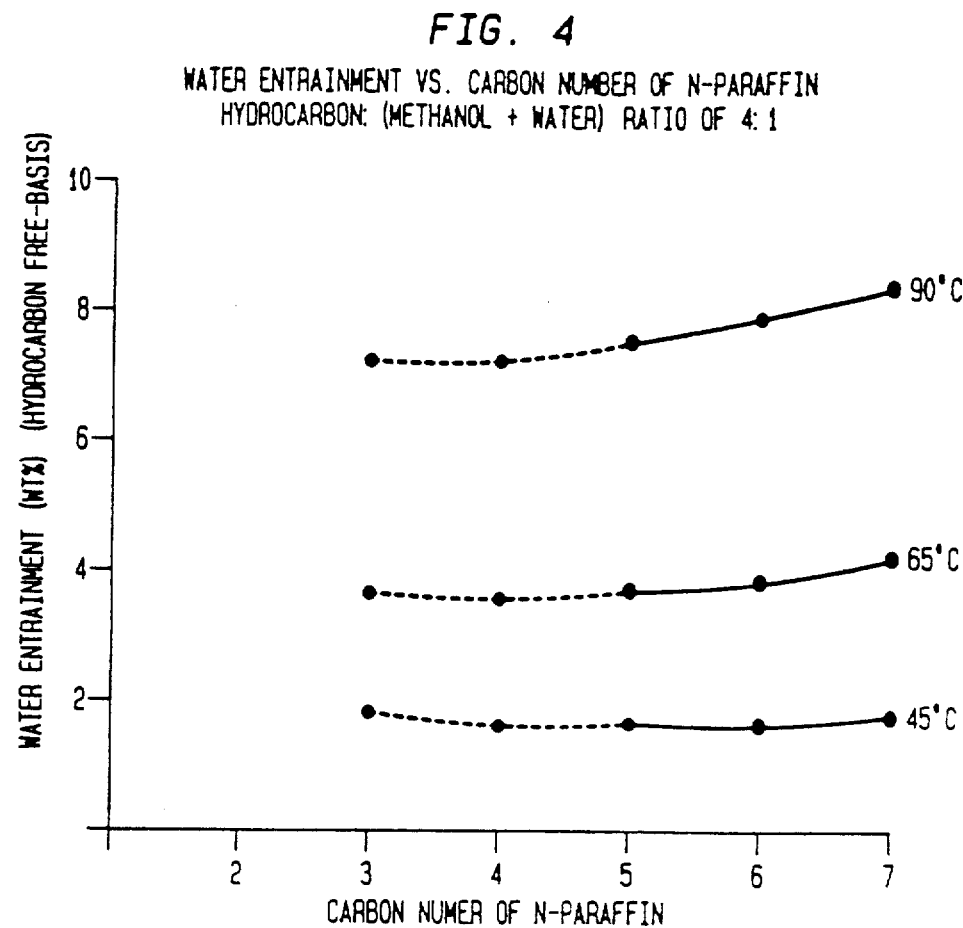
FIG. 4 is a corresponding graphic plot showing water entrainment in the extract phase for $C_3$-$C_7$ alkanes.

For this example propane is used as the hydrocarbon, as is present in a 4:1 molar ratio. Liquid propane is contacted in a liquid/liquid phase separator with crude methanol at about 43° C, (110° F.). The estimated values of methanol recovered and water entrained are determined according to FIGS. 3 and 4. This improved technique is compared to a conventional distillation of crude methanol.

TABLE 1

| | | Extractant :Feed Ratio (Mole: Mole) | | | | | |
|---|---|---|---|---|---|---|---|
| | | 1:1 | | 2:1 | | 4:1 | |
| Solvent | Temp. (F.) | Methanol Recry (wt. %) | Water Entrnmnt (wt. %) | Methanol Recry (wt. %) | Water Entrnmnt (wt. %) | Methanol Recry (wt. %) | Water Entrnmnt (wt. %) |
| Propane | 110 | 19.81 | 1.41 | 36.03 | 1.50 | 58.64 | 1.85 |
| | 150 | 20.62 | 2.82 | 36.89 | 3.16 | 59.21 | 3.75 |
| | 190 | 22.79 | 5.37 | 39.77 | 6.06 | 61.05 | 7.36 |
| n-Butane | 110 | 15.00 | 1.31 | 27.85 | 1.41 | 47.26 | 1.67 |
| | 150 | 16.36 | 2.84 | 30.02 | 3.13 | 49.92 | 3.68 |
| | 190 | 18.52 | 5.59 | 33.41 | 6.20 | 54.20 | 7.42 |
| n-Pentane | 110 | 11.23 | 1.30 | 21.35 | 1.40 | 37.93 | 1.60 |
| | 150 | 12.86 | 2.98 | 24.24 | 3.23 | 42.33 | 3.74 |
| | 190 | 14.93 | 5.96 | 27.85 | 6.50 | 47.67 | 7.63 |
| n-Hexane | 110 | 8.50 | 1.38 | 16.53 | 1.47 | 30.65 | 1.64 |
| | 150 | 10.12 | 3.24 | 19.55 | 3.46 | 35.68 | 3.93 |
| | 190 | 12.02 | 6.48 | 23.09 | 6.96 | 41.46 | 7.99 |
| n-Heptane | 110 | 6.81 | 1.55 | 13.38 | 1.62 | 25.41 | 1.79 |
| | 150 | 8.14 | 3.62 | 15.95 | 3.82 | 29.97 | 4.25 |
| | 190 | 9.79 | 7.15 | 19.13 | 7.58 | 35.57 | 8.50 |

In both cases, the same crude methanol stream is dewatered. In both cases the same amount of methanol and water is recovered (4 wt. % water on a hydrocarbon-free basis), and the feed temperature to the distillation tower was kept constant.

Table 1 shows estimated methanol recovery and water entrainment for 5 hydrocarbon solvents, at different extraction temperatures for various hydrocarbon:crude methanol ratios. These data shown graphically in FIGS. 3-4, indicate better methanol recovery with lower molecular weight hydrocarbons. At higher temperatures, recovery increases, but so does water entrainment. When two liquid phase are present, pressure appears to have no significant effect.

Table 2 indicates that reboiler duty decreases by 51%, overhead condenser duty decreases by 56%, and the distillation tower diameter decreases by 41% when extraction is used prior to distillation. Preheat of the feed or recycle $C_3$ hydrocarbon can occur even if the extraction is not performed, so it is not a dewatering process energy expense.

TABLE 2

METHANOL DISTILLATION TOWER OPERATING PARAMETERS

| | Distillation Only | Extraction/ Distillation |
|---|---|---|
| Feed | | |
| Methanol (lbmol/hr) | 16364. | 6768. |
| Water | 6080. | 5755. |
| Propane | | 216. |
| Overhead Product | | |
| Methanol (mol/hr) | 16357.10 | 6761 |
| Water | 1181.22 | 850 |
| Propane | | 216 |
| Bottoms Product | | |
| Methanol (mol/hr) | 6.90 | 6.93 |
| Water | 4898.78 | 4905 |
| Duties | | |
| Condenser (mmBtu/hr) | 423 | 186 |
| Reboiler | 361 | 177 |

REACTOR SYSTEM PROCESS CONDITIONS

The feedstock for a fixed bed MTG catalytic reactor can be the effluent from a DME dehydration reactor. In such a case, the intermediate stream is an equilibrium mixture of methanol, water and DME. If desired, complete or partial separation into constituent product streams of water, methanol, and DME may be carried out as described in U.S. Pat. No. 4,035,430 by condensation or fractionation, depending upon the degree of purity desired. Removal of at least the water is desirable because the conversion catalysts used in the fixed bed catalytic reactor usually become deactivated under hydrothermal reaction conditions encountered in the conversion. Although it is not feasible to eliminate the presence of water vapor completely from the conversion, because water is a by-product; the removal of water from the charge will lead to a reduction of the water vapor partial pressure in the conversion reactor and will, accordingly, lead to an increase in the useful life of the catalyst.

The dehydration products are passed to the fixed bed MTG reactor under conversion conditions at elevated temperature and pressure. The conversion to hydrocarbons is preferably catalyzed by a medium pore crystalline metallosilicate zeolite catalyst having Bronsted acid functionality. Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The preferred class of catalysts is characterized by a Constraint Index of 1 to 12 and a silica:alumina ratio of at least 12:1 and preferably higher e.g., 20:1 to 100:1. Preferred aluminosilicate zeolites which have the specified values of Constraint Index and silica:alumina ratio include zeolites ZSM-5, ZSM-11, ZSM-12, ZSM-35, and ZSM-48, which are described in U.S. Pat. Nos.

3,702,886 (ZSM-5), 3,709,979 (ZSM-11), 3,832,449 (ZSM-12), 4,076,842 (ZSM-23) and 4,016,245 (ZSM-35), incorporated herein by reference. The zeolite catalyst used is at least partly in the hydrogen form e.g., HZSM-5; but other cations, e.g., Periodic Groups III-–VIII or rare earth cations, may also be present. Other cations e.g., metal cations can be introduced by conventional base exchange techniques.

In this invention, the exothermic reaction can be moderated by recycling $C_3$–$C_4$ hydrocarbons employed in extracting the feedstock methanol. Rather than employing a $C_2^-$ recycled light hydrocarbon gas as the diluent, $C_3$–$C_4$ rich (LPG) recycle fraction is used. The LPG stream may comprise, on a molar basis, about 48% isobutane, about 16% propane, and about 18% n-butane, with a minor amount of olefins. The MTG reactor can be operated under process conditions that convert propane or other alkanes. Where a supply of outside propane is available, a major amount of the extractant can be comprised of recycled and makeup propane. Typically, about 95% of the LPG recycle are $C_3$–$C_7$ saturated hydrocarbons.

A major advantage of employing an LPG recycle stream is that liquid can be repumped economically in order to recycle it back to the fixed bed MTG catalytic reactor. If light hydrocarbon gas is used for the recycle, it must be recompressed at great expense. A large gas recycle compressor usually requires a source of high pressure superheated steam; whereas the $C_3$–$C_4$ recycle design demands much less energy to achieve the process reaction pressure. Another advantage of an LPG recycle versus a light gas recycle is that an increased circulation of LPG range material through the reaction zone can provide increased conversion of $C_3$–$C_4$ olefins to gasoline range hydrocarbons. The overall MTG gasoline yield would then be greater. In addition, improved selectivity toward reduced fuel gas production is obtained.

In the embodiment of FIG. 1, extracted methanol is passed to the reactor system with hydrocarbon extractant containing LPG recycle. The combined feedstock and recycle is conducted at a temperature of about 340°–345° C. (650° F.) and a pressure of about 1000–1100 kPa (154 psia) to a fixed bed MTG catalytic reactor.

Effluent from the fixed bed MTG reaction zone is passed to a heat exchange condenser and then to a separation zone without significant loss of pressure. In the separation zone the effluent stream is partitioned into three streams. Typically, the separator is operated at conditions of about 35°–40° C. (100° F.) and about 700–750 kPa (107 psia). From the separator the liquid hydrocarbon fraction is passed to a pump where it is repressurized to about 1100 kPa to 1400 kPa. From the heat exchange evaporator the partially vaporized fraction is passed to an accumulator. The accumulator is operated at about 90°–95° C. (195° F.) and about 1200–1300 kPa (186 psia). A typical liquid hydrocarbon distillation unit operation is described in Copending U.S. patent application Ser. No. 815,438, filed Dec. 31, 1985 (Owen et al), incorporated herein by reference. From the accumulator a vaporized fraction containing a major amount of $C_3$–$C_4$ saturated hydrocarbons (LPG) is passed to a zone where it is separated from LPG make. The purified LPG fraction is then conducted to a heat exchange evaporator where it is brought to a temperature of about 335° C. (636° F.) before or after mixing with feedstock.

Figure 5:
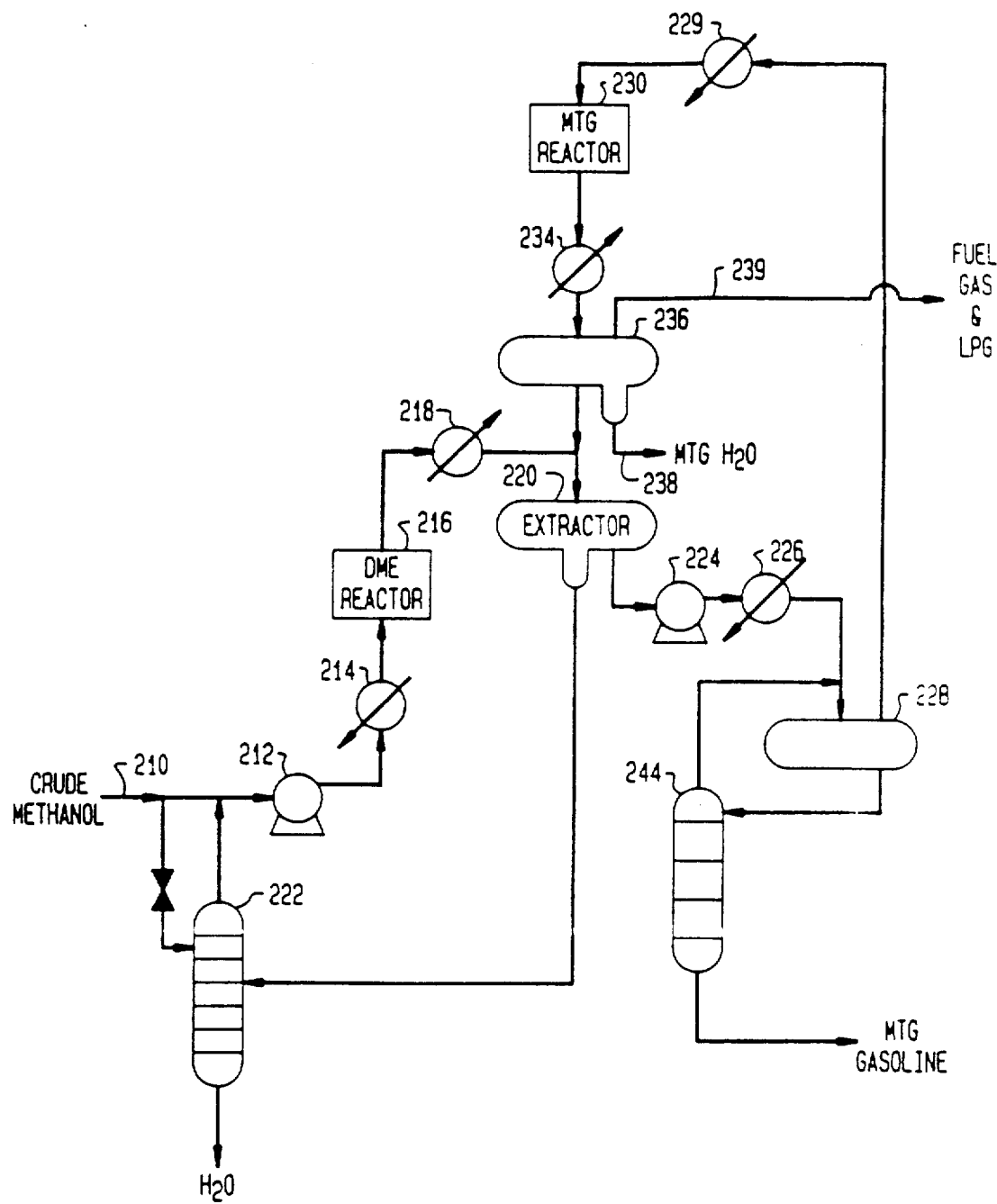
FIG. 5 is a schematic process flowsheet for an alternative embodiment of the invention using full range $C_3$+ liquid extractant.

Referring to FIG. 5 of the drawing, crude methanol (MeOH) feedstock is introduced via conduit 210 and pump 212, heated in feedstock exchanger 214, and passed to a first stage DME reactor 216, where the aqueous methanol feed is contacted at elevated temperature with a dehydration catalyst, such as gamma-alumina to provide an equilibrium mixture of methanol, water and dimethylether. After cooling this first effluent stream in heat exchanger 218, the liquid oxygenate-rich stream is contacted with a liquid hydrocarbon extractant stream rich in $C_3$–$C_{10}$ hydrocarbons (especially $C_3$–$C_7$ alkanes) in extraction unit 220, thereby transferring a major portion of the methanol and dimethyl ether oxygenates to the organic extract phase. The aqueous raffinate phase is recovered from extractor 220 and passed to distillation unit 222 for concentrating the oxygenates prior to recycling with feedstream 210. The lighter organic extract phase containing hydrocarbon extraction solvent and the major amount of feedstock methanol and dimethyl ether is recovered from extraction unit 220 and pressurized by pump means 224, passed through heat exchanger 226, and phase separator unit 228 to vaporize the oxygenates and a portion of volatile C3-C4 hydrocarbons. The oxygenate-rich vapor stream containing C3-C4 diluent is then heated in exchanger 229 and introduced at elevated temperature and process conditions suitable for conversion of substantially all of the oxygenates in contact with the MTG catalyst in reactor system 230. From the reactor system 230, the effluent product stream is passed to heat exchange condenser 234, and is passed as a three-phase mixture to a phase separator 236. The temperature and pressure of the separator are maintained such that the products are split into three separate streams. The MTG byproduct water is recovered via line 238. The light hydrocarbon gas phase is removed via line 239. The condensed liquid hydrocarbon stream from separator unit 236 is then contacted with oxygenates in extractor unit 220 to form the organic extract stream passed to phase separator 228 and further fractionated in tower 244 to provide the $C_5+$ MTG gasoline product stream.

While the invention has been described by particular examples, there is no intent to limit the inventive concept except as set forth in the following claims:

We claim:
1. A continuous feedstock extraction and reactor system for converting crude oxygenated hydrocarbon feedstock to gasoline boiling range hydrocarbons comprising:

extractor means for contacting oxygenate liquid containing a minor amount of water with a liquid hydrocarbon extraction stream under extraction conditions favorable to selective extraction of oxygenate, thereby providing an extract liquid stream rich in oxygenate and an aqueous raffinate stream lean in oxygenate;

catalytic reactor means for contacting at least a portion of the extract stream in a catalytic reaction zone with conversion catalyst under process conditions to convert substantially all oxygenate to hydrocarbons;

separation means for receiving reactor effluent to recover an aqueous liquid byproduct stream, a gaseous stream rich in $C_2^-$ hydrocarbons, a liquid product stream comprising $C_5+$ liquid hydrocarbons, and a liquid stream rich in $C_3$–$C_4$ hydrocarbons;

means for recycling at least a portion of at least one liquid phase to said extractor means for use as extraction liquid.

2. The system of claim 1 wherein the separation means recovers an extraction liquid stream from reactor effluent comprising $C_3-C_4$ and $C_5+$ hydrocarbons.

3. A continuous system for converting crude water-containing oxygenated hydrocarbon feedstock to gasoline boiling range hydrocarbons comprising:
   (a) extraction means for contacting crude oxygenate feedstock containing a minor amount of water with a liquid hydrocarbon extraction stream under extraction conditions favorable to selective extraction of the oxygenate, thereby providing an extract liquid stream rich in oxygenate and an aqueous raffinate stream lean in oxygenated hydrocarbons;
   (b) reactor means for converting the extracted oxygenate substantially free of water in a catalytic reaction zone with a solid acid oxygenate conversion catalyst at elevated temperature and pressure to convert oxygenate to hydrocarbons;
   (c) heat exhange means for cooling reactor effluent to recover an aqueous liquid byproduct stream, a light gas stream, a first liquid stream rich in $C_3-C_4$ hydrocarbons and a second liquid stream rich in $C_5+$ liquid hydrocarbons; and
   (d) means for contacting crude oxygenate feedstock with at least a portion of the first liquid stream employed as extraction liquid.

4. The system of claim 3 including means for recycling a major amount of $C_3-C_4$ hydrocarbons with extracted oxygenate to the reaction zone as a vapor stream; and wherein oxygenate is separated from the aqueous raffinate and passed to the reaction zone for conversion with the extracted oxygenate.

5. The system of claim 3 including means for distilling residual oxygenate from the aqueous raffinate stream and means for passing distilled oxygenate to said reaction zone.

6. A continuous system for converting crude aqueous methanol-containing oxygenated hydrocarbon feedstock to gasoline boiling range hydrocarbons comprising:
   (a) extraction means for contacting crude oxygenate feedstock containing a minor amount of water with a liquid hydrocarbon extraction stream under extraction conditions favorable to selective extraction of the oxygenate, thereby providing an extract liquid stream rich in oxygenate and an aqueous raffinate stream lean in oxygenated hydrocarbons;
   (b) reactor means for converting the extracted oxygenate substantially free of water in a catalytic reaction zone with a solid acid oxygenate conversion catalyst at elevated temperature and pressure to convert oxygenate to hydrocarbons;
   (c) heat exchange means for cooling reactor effluent to recover an aqueous liquid byproduct stream, a light gas stream, a first liquid stream rich in $C_3-C_4$ hydrocarbons and a second liquid stream rich in $C_5+$ liquid hydrocarbons; and
   (d) means for contacting crude oxygenate feedstock with extraction liquid containing at least a portion of the second liquid stream.

* * * * *

UNITED STATES PATENT AND TRADEMARK OFFICE
CERTIFICATE OF CORRECTION

PATENT NO. : 4,857,667

DATED : August 15, 1989

INVENTOR(S) : Mohsen N. Harandi, et al

It is certified that error appears in the above-identified patent and that said Letters Patent is hereby corrected as shown below:

The title page should be deleted to appear as per attached title page.

The sheets of drawings consisting of Figs. 1-5 should be added as per attached sheet.

Signed and Sealed this

Twelfth Day of March, 1991

Attest:

HARRY F. MANBECK, JR.

Attesting Officer

Commissioner of Patents and Trademarks

United States Patent [19]

Harandi et al.

[11] Patent Number: 4,857,667
[45] Date of Patent: Aug. 15, 1989

[54] SYSTEM FOR CONVERSION OF CRUDE OXYGENATE TO GASOLINE WITH FEEDSTOCK EXTRACTION

[75] Inventors: Mohsen N. Harandi, Sewell; Hartley Owen, Belle Mead, both of N.J.

[73] Assignee: Mobil Oil Corporation, New York, N.Y.

[21] Appl. No.: 105,425

[22] Filed: Oct. 7, 1987

Related U.S. Application Data

[63] Continuation-in-part of Ser. No. 43,718, Apr. 29, 1987, Pat. No. 4,709,113.

[51] Int. Cl.$^4$ .................................................. C07C 1/20
[52] U.S. Cl. ......................................... 585/403; 585/503; 585/469; 585/636; 585/640; 585/920; 585/921; 585/408
[58] Field of Search ............... 585/640, 733, 469, 639, 585/408, 754, 403, 503, 920, 921, 636; 422/211, 234, 235, 225

[56] References Cited

U.S. PATENT DOCUMENTS

| | | | |
|---|---|---|---|
| 4,497,968 | 2/1985 | Wright et al. | 585/304 |
| 4,513,156 | 4/1985 | Tabak | 585/329 |
| 4,709,113 | 11/1987 | Harandi et al. | 585/640 |
| 4,788,042 | 11/1988 | Marsh et al. | 585/403 |
| 4,788,369 | 11/1988 | Marsh et al. | 585/403 |

*Primary Examiner*—Asok Pal
*Attorney, Agent, or Firm*—Alexander J. McKillop; Charles J. Speciale; L. G. Wise

[57] ABSTRACT

Apparatus for converting crude aqueous oxygenate feedstock, such methanol or the like, to liquid hydrocarbons in contact with a medium pore shape selective crystalline acid zeolite catalyst, such as HZSM-5. In a preferred embodiment, the novel technique comprises means for: (a) contacting a crude methanol feedstock containing a minor amount of water with a liquid hydrocarbon extraction stream under extraction conditions favorable to selective extraction of the methanol, thereby providing an extract liquid stream rich in methanol and an aqueous raffinate stream lean in methanol; (b) charging the extracted methanol substantially free of water to said reaction zone under process conditions to convert substantially all methanol to hydrocarbons; (c) cooling reaction effluent to recover aqueous liquid by-product stream, gas rich in $C_2{}^-$ hydrocarbons, liquid rich in $C_3$–$C_4$ hydrocarbons and $C_5{}^+$ liquid hydrocarbons; and (d) contacting crude methanol feedstock with at least a portion of the liquid hydrocarbons employed as extraction liquid.

6 Claims, 5 Drawing Sheets

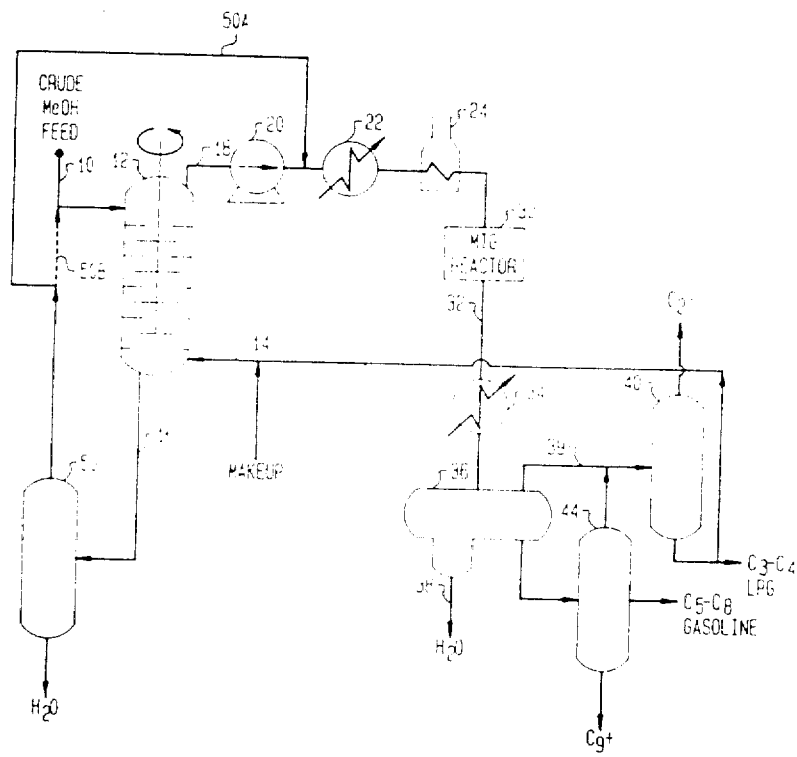

FIG. 1